US009194864B2

(12) United States Patent
Nielsen et al.

(10) Patent No.: US 9,194,864 B2
(45) Date of Patent: Nov. 24, 2015

(54) SCREENING METHODS EMPLOYING INSECTS WITH BLOOD BRAIN BARRIER

(75) Inventors: Peter Aadal Nielsen, Oxie (SE); Gunnar Andersson, Roestaanga (SE)

(73) Assignee: Entomopharm ApS, Odense SV (DK)

( * ) Notice: Subject to any disclaimer, the term of this patent is extended or adjusted under 35 U.S.C. 154(b) by 0 days.

(21) Appl. No.: 13/060,619

(22) PCT Filed: Sep. 16, 2009

(86) PCT No.: PCT/EP2009/062023
§ 371 (c)(1),
(2), (4) Date: Mar. 30, 2011

(87) PCT Pub. No.: WO2010/031794
PCT Pub. Date: Mar. 25, 2010

(65) Prior Publication Data
US 2011/0171682 A1    Jul. 14, 2011

Related U.S. Application Data

(60) Provisional application No. 61/098,803, filed on Sep. 22, 2008.

(51) Int. Cl.
*G01N 33/50*        (2006.01)
(52) U.S. Cl.
CPC .................................. *G01N 33/5085* (2013.01)
(58) Field of Classification Search
CPC ....................... G01N 33/5085; C12Q 2600/112
USPC .......................................................... 435/30
See application file for complete search history.

(56) References Cited

U.S. PATENT DOCUMENTS

| 7,332,159 B2 | 2/2008 | Labhasetwar et al. |
| 2005/0132425 A1 | 6/2005 | Lowe et al. |
| 2005/0214221 A1 | 9/2005 | Poss et al. |
| 2008/0025959 A1* | 1/2008 | Daneman et al. ............ 424/94.1 |

FOREIGN PATENT DOCUMENTS

| EP | 1 644 733 | 2/2005 |
| WO | WO 2004/006854 A2 | 1/2004 |
| WO | WO 2010/031794 | 3/2010 |
| WO | WO 2011/018446 | 2/2011 |

OTHER PUBLICATIONS

Mayer et al. Evolutionary conservation of vertebrate blood-brain barrier chemoprotective mechanisms in *Drosophila*. The Journal of Neuroscience. 2009:29(11);3538-3550.*
Mokri-Moayyed et al. Development of a novel ex vivo insect model for studying virulence determinants of *Escherichia coli* K1. Journal of Medical Microbiology. 2008;57:106-110.*
Garberg et al. In vitro models for the blood-brain barrier. Toxicology in Vitro. 2005;19:299-334.*
Carlson et al. Blood barriers of the insect. Annu. Rev. Entomol. 2000;45:151-174.*
Josserand et al. Evaluation of drug penetration into the brain: a double study by in vivo imaging with positron emission tomography and using an in vitro model of the human blood-brain barrier. The Journal of Pharmacology and Experimental Therapeutics. 2006;316(1):79-86.*
Carlson et al., "Blood barriers of the insect," *Annu. Rev. Entemol.* (2000) 45: 151-174.
Fortini et al., "Modeling human neurodegenerative diseases in *Drosophilia*," *TIG* (2000) 16 (4): 161-167.
Khan et al., "Novel model to study virulence determinants of *Escherichia coli* K1," *Infection and Immunity* (2007) 75 (12): 5735-5739. XP002557533.
Marsh et al., "Can flies help humans treat neurodegenerative diseases?" *BioEssays* (2004) 26: 485-496.
Marsh et al., "*Drosophilia* in the study of neurodegenerative disease," *Neuron* (2006) 52: 169-178. XP002557534.
Parker et al., "Roles of glia in the *Drosophilia* nervous system," *Seminars in Cell & Developmental Biology* (2006) 17: 66-77.
Sarantseva et al., "Protein transduction domain peptide mediates delivery to the brain via the blood-brain barrier in *Drosophilia melanogaster*," *Biochemistry (Moscow) Suppl Series B: Biomedical Chemistry* (2009) 3 (2): 145-155. XP002557535.
Wolf et al., "Invertebrate models of drug abuse," *J. Neurobiol.* (2003) 54: 161-178.
Form PCT/ISA/210 for corresponding International Application PCT/EP2009/062023.
Form PCT/ISA/220 for corresponding International Application PCT/EP2009/062023.
Form PCT/ISA/237 for corresponding International Application PCT/EP2009/062023.
Di et al., "Evidence-based approach to assess passive diffusion and carrier-mediated drug transport," *Drug Discovery Today*, vol. 17, No. 15/16, 2012, pp. 905-912.
Liu et al., "Progress in Brain Penetration Evaluation in Drug Discovery and Development," *The Journal of Pharmacology and Experimental Therapeutics*, vol. 325, No. 2, 2008, pp. 349-356.

(Continued)

*Primary Examiner* — Ruth Davis
*Assistant Examiner* — Lynn Y Fan
(74) *Attorney, Agent, or Firm* — Merchant & Gould P.C.

(57) ABSTRACT

There is provided insect models that are aimed to reflect vertebrate blood-brain barrier (BBB) penetration. Investigation of BBB penetration is extremely important in drug discovery; successful CNS drugs have to cross the BBB, while BBB penetration may cause unwanted side effects for peripheral acting drugs. Specifically, the present invention relates to the use of insects in screening for substances with a biological effect on the brain or central nervous system and/or effect on a disease or disorder of the brain or central nervous system. It further relates to use of such insects in screening for substances that have a desired biological activity and which do not cross the blood brain barrier.

9 Claims, No Drawings

(56) References Cited

OTHER PUBLICATIONS

Mortazavi et al., "*Acanthamoeba* produces disseminated infection in locusts and traverses the locust blood-brain barrier to invade the central nervous system," *BMC Microbiology*, vol. 10, No. 186, 2010, pp. 1-9.
Pardridge, "Blood-brain barrier delivery," *Drug Discovery Today*, vol. 12, No. 1/2, 2007, pp. 55-61.
Siddiqui et al., "Next generation of non-mammalian blood-brain barrier models to study parasitic infections of the central nervous system," *Virulence*, vol. 3, No. 2, 2012, pp. 159-163.
Summerfield et al., "Central Nervous System Drug Disposition: The Relationship between in Situ Brain Permeability and Brain Free Fraction",*The Journal of Pharmacology and Experimental Therapeutics*, vol. 322, No. 1, 2007, pp. 205-213.
Kim et al., "Blood-Brain Barrier Permeability during the Development of Experimental Bacterial Meningitis in the Rat", Experimental Neurology, 145:253-257 (1997).
Neuwelt et al., "Cerebrovascular permeability and delivery of gentamicin to normal brain and experimental brain abscess in rates", J. Neurosurg, 61:430-439 (Sep. 1984).
Strausbaugh et al., "Effect of Osmotic Blood-Brain Barrier Disruption on Gentamicin Penetration into the Cerebrospinal Fluid and Brains of Normal Rabbits", Antimicrobial Agents and Chemotherapy, 24(2):147-150 (Aug. 1983).
Williamson, et al., "Preparation of Developing and Adult *Drosophila* Brains and Retinae for Live Imaging," Journal of Visualized Experiments, (2010), pp. 1-5.
Nielsen, et al. "Models for predicting blood-brain barrier permeation," Drug Discover Today, vol. 16, Nos. 11/12, (Jun. 2011), pp. 472-475.
International Preliminary Report on Patentablility, International Appln. No. PCT/DK2012/050460, dated Feb. 4, 2013.
Banerjee et al., "Neuron-Glial Interactions in Blood-Brain Barrier Formation," Annual Review of Neuroscience, vol. 30, (2007), pp. 235-258.
International Search Report, International Application No. PCT/EP2009/062023, dated Dec. 22, 2009.
Hamamoto et al., "Silkworm as a model animal to evaluate drug candidate toxicity and metabolism", Comparative Biochemistry and Physiology, Part C, 149 (2009), 334-339.
He et al., "Benzo(a)pyrene toxicokinetics in the cricket following injection into the haemolymph", Environmental Toxicology and Pharmacology 6 (1998), 81-89.
Johny et al., "New Insect System for Testing Antibiotics", The Journal of Parasitology, vol. 93, No. 6, Dec. 2007, pp. 1505-1511.
Juang et al., "A blood-brain barrier without tight junctions in the fly central nervous system in the early postembryonic stage", Cell & Tissue Research (1992), 270: 95-103.
PCT/ISA/237, International Preliminary Report on Patentability, Written Opinion, PCT/DK2011/050367, dated Jul. 2011.
International Search Report from International Application No. PCT/DK2011/050367,dated Jan. 16, 2012.
Stork et al., Organization and Function of the Blood-Brain Barrier in *Droscophila*, The Journal of Neuroscience, 28(3): 587-597, Jan. 16, 2008.
Michaelis et al., Covalent Linkage of Apolipoprotein E to Albumin-Nanoparticles Strongly Enhances Drug Transport into Brain, The Journal of Pharmacology and Experimental Therapeutics, 317:1246-1253, (2006).
Gullan et al., The Insects: An Outline of Entomology, pp. 30-37, 56-58,Third Edition, Blackwell Publishing, (2005).
International Preliminary Report on Patentability, International Appln. No. PCT/EP2009/062023, dated Jan. 5, 2011.
Demand under Article 31, International Appln. No. PCT/EP2009/062023, dated Jun. 30, 2010.
Busch et al., "A Map of Octopaminergic Neurons in the Drosophilia Brain", *The Journal of Comparative Neurology*, vol. 513, 2009, pp. 643-667.
Drobne et al., "In vivo screening to determine hazards of nanoparticles: Nanosized $TiO_2$", *Environmental Pollution*, vol. 157, 2009, pp. 1157-1164.
Fischer et al., "Nanotoxicity: the growing need for in vivo study", *Current Opinion in Biotechnology*, vol. 18, 2007, pp. 565-571.
International Search Report and Written Opinion for International Application PCT/EP2010/061596 mailed Oct. 6, 2010.
International Search Report and Written Opinion for International Application No. PCT/Ep2010/061585 mailed Nov. 8, 2010.
Jeibmann et al., "*Drosophila melanogaster* as a Model Organism of Brain Diseases", *International Journal of Molecular Science*, vol. 10, 2009, pp. 407-440.
Mortazavi et al., "Novel model for the in vivo study of central nervous system infection due to *Acanthamoeba* spp. (T4 genotype)", *Journal of Medical Microbiology*, vol. 58, 2009, pp. 503-508.
Nielsen et al., "Models for predicting blood-brain barrier permeation", *Drug Discovery Today*, vol. 16, No. 11/12, (2011), pp. 472-475.
Non-Final Office Action from U.S. Appl. No. 13/387,094 mailed Feb. 12, 2013.
Olivier, "Drug Transport to Brain with Targeted Nanoparticles", *NeuroRx*, vol. 2, No. 1, 2005, pp. 108-119.
Restriction Requirement Office Action from U.S. Appl. No. 13/387,094 mailed Sep. 24, 2012.
Thomas, "Insect Blood-brain Barrier: A Radioisotope Study of the Kinetics of Exchange of a Liposoluble Molecule (n-Butanol)", *J. exp. Biol.*, vol. 64, (1976) pp. 119-130.
Warheit et al., "Development of a base set of toxicity tests using ultrafine $TiO_2$ particles as a component of nanoparticle risk management", *Toxicology Letters*, vol. 171, 2007, pp. 99-110.
Wilson, "Brain targeting PBCA nanoparticles and the blood-brain barrier", *Nanomedicine*, vol. 4, No. 5, 2009, pp. 499-502.

* cited by examiner

SCREENING METHODS EMPLOYING INSECTS WITH BLOOD BRAIN BARRIER

This application is a National Stage Application of PCT/EP2009/062023, filed 16 Sep. 2009, which claims benefit of Ser. No. 61/098,803, filed 22 Sep. 2008 in the United States and which applications are incorporated herein by reference. To the extent appropriate, a claim of priority is made to each of the above disclosed applications.

FIELD OF THE INVENTION

The present invention is directed to insect models that are related to reflect vertebrate blood-brain barrier (BBB) penetration. Investigation of BBB penetration is extremely important in drug discovery; successful CNS drugs have to cross the BBB, while BBB penetration may cause unwanted side effects for peripheral acting drugs. Specifically, the present invention relates to the use of insects in screening for substances with a biological effect on the brain or central nervous system and/or effect on a disease or disorder of the brain or central nervous system. It further relates to use of such insects in screening for substances that have a desired biological activity and which do not cross the blood brain barrier.

BACKGROUND OF THE INVENTION

Drug discovery is a costly affair where one of the major expenses in terms of money and time is the in vivo studies. In order to reduce these costs a large number of in vitro models are developed and applied as filters to select the most suitable compounds for the in vivo studies. However, in vitro models are often too simplified and may as such be misleading in the decision-making process. Hence, there is a demand for intermediate models that are more reliable than in vitro models and at the same time faster and cheaper than traditional vertebrate in vivo models. Insects may serve this function and fruit flies are currently used as intermediate pharmacodynamic (PD) models by EnVivo Pharmaceuticals Inc., which develops CNS drugs.

There are various problems with existing in vitro testing. It is impossible to run in vitro assays to account for all biological events that occur in vivo. There are biological events that are not yet understood or shortcomings in the existing in vitro assays, e.g. assays may lack important features that are present in vivo, including active transporter molecules, metabolic enzymes, or even unforeseen biological events. Despite the obvious shortcomings, the in vitro models are heavily used in the drug discovery process where most pharmaceutical companies use large batteries of in vitro screens.

Testing compounds in a large number of in vitro assays may not always reflect the in vivo behavior. In fact, it is not unusual that compounds that have acceptable in vitro profiles turn out to have inadequate in vivo profiles. On the contrary, compounds may be discarded for wrong reasons. Thus, there is a requirement for intermediate in vitro/in vivo models, which could support the drug discovery research with improved data and hereby reduce the number of expensive in vivo experiments.

In vitro models are used with the supposition that each of the models reflects one single and isolated in vivo biological event. However, the large number of in vitro models that are used in the discovery phase (Ruiz-Garcia et al. 2007) are aimed at reflecting the complexity of the in vivo biology where numerous biological events take place in multiple compartments. A major limitation by using many in vitro models is the lack of interplay between different biological events and the interplay between different compartments. However, one major advantage by using insects as intermediate models is that these models fulfill the requirement of a complex interplay not only between different components of the brain barrier structure but also between the different compartments that appear in the insects since they are living species with compartments that to a large extent are similar to vertebrate.

The vertebrate blood-brain barrier (BBB) represents the physiological barrier between the brain tissue and blood vessels, which restricts the exchange of solutes and regulates absorption of exogenic agents (e.g. drugs) from the blood into the brain. The function of the central nervous system (CNS) requires a highly regulated extra-cellular environment. Anatomically the BBB in vertebrates is comprised of microvascular endothelia cells interconnected via highly specialized tight junctions (TJs), which provide a diffusion barrier and thus play a central role for permeability. Recently identified components of TJs include the claudins, a family of four-transmembrane-span proteins that are suggested to be responsible for the barrier-function of TJs (Turksen and Troy 2004). Penetration of BBB is one of the major hurdles in the development of successful CNS drugs. On the other hand, when penetration of the BBB occurs it may cause unwanted side effects for peripheral acting drugs (Schinkel 1999) (for review see Pard ridge 2002).

BBB penetration is usually classified as chemistry- or biology-based. The chemistry-based penetration is linked to the lipid mediated passive diffusion, which depends on physiochemical properties of the molecule, i.e. small hydrophobic molecules tend to penetrate the BBB more readily than large and hydrophilic molecules. The biology-based penetration involves compounds that are substrates for the endogenous BBB influx or efflux transport systems, e.g. many small molecules (e.g. drugs) have shown to be substrates for the P-glycoprotein (P-gp) transporter. The P-gp's are transporter proteins located in the walls of the cells that make up the BBB (Schinkel 1999) and they are conserved among taxa as diverse as protozoa, plants, insects and mammals (in Gaertner et. al. 1998). P-gp's are present in many cell-types and they play important roles in drug absorption, disposition, metabolism, and toxicity (Xia et al. 2006).

Obviously, it is crucial to have an understanding of the BBB penetration in drug discovery projects and preferably, this should be obtained without using excessive number of in vivo studies. Consequently, several in vitro BBB absorption models are developed to predict the in vivo behaviour of test compounds. However, even complex in vitro models which include the P-gp transporter systems (Di and Kerns 2003, Summerfield et al. 2005) seem not to meet the intricate complexity of the TJs and therefore may not describe the in vivo behavior very well. This is strongly indicated in an extensive BBB absorption study, in which 22 compounds were tested in ten different in vitro BBB absorption models (Garberg 2005). None of the ten models showed any correlation between in vitro and in vivo permeability. This indicates that specific BBB models not necessarily provide better prediction than non-BBB derived models. Furthermore, it was suggested that protein binding, blood-flow, metabolic stability and lipophilicity, as well as affinity for other transporters in the BBB are factors needed to be considered when predictions of in vivo brain distribution is to be made. Consequently, it seems as in vitro models are mainly suited for qualitative measurements of compounds that penetrates BBB by passive diffusion or compounds that undergo efflux via the P-gp transporter (Garberg 2005).

Certain invertebrates have served as useful models for understanding many different biological processes. Especially the fruit fly, *Drosophila melanogaster* is a well-recognized model research organism, which have made significant contributions to the understanding of genetics, neurobiology, molecular biology etc. (Gullan and Cranston 2000). Generally, insects and vertebrates have many physiological features in common. They are multi cell organisms with complex compartmentalized nervous systems for specialized functions like vision, olfaction, learning, and memory. The nervous systems of the insects respond physiologically in similar ways as in vertebrates with many identical neurohormones and receptors. Insects have avascular nervous systems in which hemolymph bathes all outer surfaces of ganglia and nerves. Therefore, many insects require a sophisticated BBB system to protect their CNS from plant-derived neurotoxins and to maintain an appropriate ionic microenvironment of the neurons. In fact, also in insects a sophisticated BBB system has been an evolutionary advantage. In insects this BBB is mainly based on the glia cell system which certainly shifted to the endothelial system as a response to the increased importance of the microvasculature in the vertebrate brain. In support of this view is the appearance of the glia system in elasmobranch fish and the remnants of the glia barrier in modern mammalian CNS. Thus insects possess a BBB which is an important component in the ensheathment of the nervous system. The BBB:s in insects are highly sophisticated but varies in structure between different insect orders. Thus insects with highly sophisticated brain barriers with complex integrative components that mimic the vertebrate barriers will be excellent models for documentation of penetration of various molecules through this structure.

US20050132425A1 discloses a transgenic fly that expresses the Italian mutant version of the human Abeta42 peptide of human amyloid-beta precursor protein (APP), and a double transgenic fly that expresses both the Tau protein and the human Abeta42$_{Italian}$ peptide of human amyloid-beta precursor protein (APP). The transgenic flies provide for models of neurodegenerative disorders, such as Alzheimer's disease. US20050132425A1 further discloses methods for identifying genetic modifiers, as well as screening methods to identify therapeutic compounds to treat neurodegenerative disorders using the transgenic flies.

WO04006854A2 discloses a method for screening for the effect of a test agent on a population of insects comprising the steps of providing a population of specimen, administering at least one test agent to the population, creating a digitized movie showing the movements of the insects, measuring at least one trait of the insects of the population with the effect of the test agent. The document also provides a method for preparing a medicament useful for the treatment of a mammalian disease.

Marsh and Thompson (Marsh and Thompson 2006) teach that insects are very useful as model systems due to simplicity combined with fast reproducibility. Some of the models (with *Drosophila*) have demonstrated their efficiency for testing relevant drugs and revealed concordance of drug efficacy in flies and mammals for diseases like Huntingtons's, Parkinson's and Alzheimer's.

Marsh and Thompson (Marsh and Thompson 2004) suggest that the dominant neurodegenerative diseases of man can be faithfully modelled in insects, such as *Drosophila* (fruitfly), since they exhibit the key features of these diseases such as slowly progressing degeneration, late onset, formation of abnormal protein aggregates etc. According to the authors the ability to manipulate such engineered organisms allows pathogenic mechanisms to be identified and potential pharmacologic regimens to be rapidly tested. The authors suggest that the excellent agreement to date of pharmacologic treatments that are effective in suppressing pathology in both flies and in mice gives growing confidence that invertebrate model organisms can productively speed the identification of agents that are likely to be effective at treating diseases in mammals.

As appears from the above mentioned literature the prior art is primarily directed to the testing of compounds in flies (*Drosophila*) for use in the treatment of human neurodegenerative diseases. However, there is still a need to identify appropriate screening models beyond the commonly used in vitro testing methods to determine/assess blood-brain barrier penetration of drugs. In this regard it should be borne in mind that flies have septate junctions and not tight junctions like vertebrate and locust, moth and cockroaches.

There is an urgent need for more sophisticated screening models in drug discovery but also in testing of CNS toxicity of chemicals on market with less known effects on brain function.

Thus, in drug discovery there is:
a) a need for efficient screening of compounds aimed at targets within the CNS system. This screening is preferentially performed in insect models with intact BBB function and will contribute to a positive selection of compounds penetrating the BBB. Such screening comprises low molecular weight compounds within a number of indications (e.g. pain, epilepsy, Parkinson, schizophrenia, Alzheimer, sleep disorders, anxiety, depression, eating disorders, drug abuse including smoking).
b) a need for efficient screening of compound which are targeted for efficacy outside CNS and when penetrating CNS may induce non acceptable side effects.
c) a need for efficient screening in insect models characterized by selective changes in the function of the BBB. Such screening comprises low to very high molecular weight compounds or peptides or macromolecules in diseases characterized by deteriorated BBB function (e.g. ischemic stroke, traumatic brain injury, drug abuse, neurodegenerative diseases like Parkinson and Alzheimer, epilepsy, infections, inflammation like meningitis and MS, HIV).

There is also a need for screening of chemical compounds on the market, which has not been classified or documented for there potential neurotoxicity.

SUMMARY OF THE INVENTION

The overall object of the present invention is to develop insect screening models to determine/assess blood-brain barrier penetration in vertebrates, such as mammals, preferably humans, of different chemical compounds in order to improve the compound screening procedures/processes in the early drug discovery process. This object offers many advantages relative to prior technologies since insect models are more reliable tools for the decision-making process than the existing in vitro models, and will speed up the drug screening process and reduce the late phase attrition rate. Moreover, it will reduce the number of mammals sacrificed during the drug discovery phase.

The present inventors have surprisingly found that the blood-brain barrier (BBB) in insects selected from the group consisting of cockroaches, locusts and moths has more in common with BBB of mammals than previously assumed. It has been found that the barrier system in these insects is made up of TJs while in the flies (eg *Drosophila*) its made up of septate junctions (SJs) (Banerjee and Baht 2007). The insects of the present invention may therefore serve as an intermediate model for determination of BBB penetration of chemical substances.

The present invention is thus able to provide for the first time rational strategies for screening compounds for neurological indications, as well as generating in a simple in vivo system for determining a compound's brain penetration. The present invention is also able to provide a rational screening of compounds in insect models mimicking BBB dysfunction as a consequence of neurological disorders.

Drug discovery is a long and costly process, requiring vast amount of chemical and biological resources. In the present invention the possibilities to use insects as model systems have been thoroughly exploited in order to improve compound selection processes and reduce the costs during the drug discovery phase. Based on recent discoveries the inventors have fully contemplated that insect models of the present invention provide a better foundation than the existing in vitro models for selection of compounds to be tested in vertebrates.

In one aspect, the invention provides a method for screening for the BBB penetration of a test agent, said method comprises the steps of:
administering the test agent to insects selected from the orders consisting of Blattodea, Acridoidea, Cheleutoptera, Brachycera and Lepidoptera,
incubating the insects for a period of between 0.05 hour and 72 hours,
dissecting brains from the insects,
measuring the concentration of the test agent in the dissected brains.

In a preferred embodiment of the present invention the insects are selected from the Acridoidea (locusts) and Blattodea (cockroaches) orders.

In another preferred embodiment of the present invention the insects are incubated for a period of between 0.5 hour and 5 hours before dissecting the brains from the insects with a view of quantifying the concentration of the administered test agent in the brains.

The dissection of the brains should preferably be performed immediately after sacrificing the insects. Alternatively, the brains are dissected and removed from living insects.

Preferably the dissected brains are homogenized and eventually lysed in order to obtain a homogeneous liquid reflecting the composition of the brains. The liquid is centrifuged and the supernatant stored until analysis. The further analysis of the liquid may be performed by virtue of liquid chromatography, possibly with mass spectrometric detection of the eluted compounds.

In further embodiments, the invention provides for screening methods for agents that exert a desired biological activity in the body but also an undesired biological activity on a target that exists in the brain, central nervous system and/or eye.

Thus, a screening method of the present invention may be employed to determine biological activity of a test substance and to determine/assess ability or inability of the test substance to cross the blood brain barrier, in particular the human blood brain barrier, e.g. by determining whether or not the substance appears to any significant extent within the brain, central nervous system or eye when not administered directly to these tissues.

In various aspects and embodiments the present invention provides the subject-matter set out in the claims below.

The invention is generally applicable to any of a drug discovery programs targeting a variety of diseases and disorders, specifically degenerative disorders, including: Parkinson's Disease, Alzheimer's Disease, Huntington's Disease, Diseases with motor neuron inclusions, Tauopathies, Corticobasal degeneration; Neuropsychiatric disorders, including: Depression Bipolar disease, Schizophrenia, Anxiety, and Aggression. Moreover, the invention is applicable for drug discovery programs targeting peripheral targets where no CNS driven side effect can be tolerated or screening of chemical compounds which effects on CNS functions is unknown.

Thus, the invention is equally applicable to screening for agents which exert a biological effect that alters an activity or function in the central nervous system, brain or eye, whether normal or subject to a disease or disorder, as to screening for agents which exert a biological effect that is ameliorative of a sign or symptom of a disease or disorder. Moreover, the present invention offers the possibility to test whether or not peripherically acting drugs and toxic agents, such as pesticides, unintentionally penetrate the BBB.

Following identification of a test substance with desired biological activity using a screening method in accordance with any aspect or embodiment of the present invention the test substance may be formulated into a composition comprising at least one additional component, for example a pharmaceutically acceptable vehicle, carrier or excipient.

DETAILED DESCRIPTION OF THE INVENTION

The present invention provides new methodology for screening for BBB penetration of chemical substances, which enter the blood stream. The invention is generally particular useful for high throughput screening for agents developed in drug discovery programs targeting a variety of diseases and disorders, specifically degenerative disorders, including: Parkinson's Disease, Alzheimer's Disease, Huntington's Disease, Diseases with motor neuron inclusions, Tauopathies, Corticobasal degeneration Neuropsychiatric disorders, including: Depression Bipolar disease, Schizophrenia, Anxiety, and Aggression. Moreover, the invention is applicable for drug discovery programs targeting peripherical targets where no CNS driven side effect can be tolerated. Moreover, the present invention is applicable in the screening of agents developed in drug discovery programs targeting eating disorders and sleep disorders etc.

The present invention relates to but is not restricted to the use of insects selected from the following orders: (Taxonomy according to: Djurens Värld, Ed B. Hanström; Förlagshuset Norden A B, Malmö, 1964):

| Order | Suborder/family | Comment |
|---|---|---|
| Dictyoptera | Blattodea | Cockroach |
|  | Mantodea |  |
| Orthoptera | Grylloidea | Crickets |
|  | Acridoidea | Grasshoppers |
| Cheleutoptera |  | Stick insects |
| Lepidoptera |  | Moths |
| Hymenoptera | Formicoidea | Ants |
|  | Vespoidea | Wasps |
|  | Apoidea | Bee like hymenopterans |
|  | Bombinae | Bumble-bees |
|  | Apine | Proper bees |
| Odonata |  | Dragonflies |
| Diptera | Nematocera | Mosquitos |
|  | Brachycera | Flies E. g Drosophila |

In particular the invention relates to insect species selected from Blattodea, Acridoidea, Cheleutoptera, Brachycera and Lepidoptera and most particular to the Acridoidea (*Locusta migratoria* and *Schistocera gregaria*).

The invention will also relate to the following orders comprising insect species relevant for the screening method:

| Order | Suborder/family | Comment |
|---|---|---|
| Ephemerida | | Mayflies |
| Plecoptera | | |
| Dermoptera | Forficuloidea | Earwigs |
| Homoptera | Cicadinea | Cicadas |
| | Aphidine | Plant-louse |
| Heteroptera | | Hemipteran |
| Coleoptera | | Beetles |
| Trichoptera | | Caddis fly |

The present invention preferably uses large insects, such as the migratoty locust, *Locusta migratoria* and the desert locust, *Schistocera gregaria* or cockroach where it is feasible to feed and inject drugs and subsequently take hemolymph samples and dissect brain tissues, for analyses. The locust has been used to develop screening models to determine BBB penetration of different therapeutic drugs and compare this model with existing literature data from conventional in vivo vertebrate studies.

Drug discovery is a long and costly process, requiring vast amount of chemical and biological resources. In the present invention specific insects are used as model systems in order to improve compound selection processes and reduce the costs during the drug discovery phase. Based on experiments it has surprisingly been found that the insect models of the present invention provide a better foundation than the existing in vitro models for selection of compounds to be tested in vertebrates.

Accordingly, the present invention focuses on insect models that are aimed to reflect vertebrate blood-brain barrier (BBB) penetration. As indicated above the investigation of BBB penetration is extremely important in drug discovery; successful CNS drugs have to cross the BBB, while BBB penetration may cause unwanted side effects for peripheral acting drugs.

In accordance with a preferred embodiment of the present invention the migratoty locust, *Locusta migratoria* and/or the desert locust, *Schistocera gregaria*, is used since it is easy to breed and it is a relatively large insect (40-60 mm long, weight: approx. 2 g, hemolymph volume: approx. 300 µL, brain weight: approx. 2 mg).

The invention is described in detail in the following sections, however, a brief introductory description of one illustrative embodiment will assist the reader in the understanding of the invention. However, this introduction describing a particular embodiment is not to be construed as limiting the invention.

The application of a test substance to insects of the present invention in a screening method may be as follows, in accordance with a preferred embodiment of the present invention.

EXAMPLES

In a preferred embodiment of the present invention the insects are selected from the order Acridoidea and specifically *Locusta migratoria* and *Schistocera gregaria* are used. The insects may be obtained from local suppliers or bred in house and maintained and fed according to Goldworthy et al. (2003). Test compounds are administrated into the haemolymph as described by Goldworthy et al. (2003) or administered orally in the food or by use of a probe. For quantitative determination of brain drug concentration the brains are dissected according to Mokri-Moayyed et al. (2008), washed, snap-frozen and stored until analyses. At analysis the brains are homogenised/vortexed and centrifuged. The drug containing supernatant is analysed for its drug concentration by HPLC, LC/MSMS or other relevant methods. The effect of drug treatment may be documented by recording the pharmacological effects on behaviour or by use of recordings of central nervous system nerve signalling.

Example A

20 µl of a 9.8 mg/ml solution of mianserin was injected into 6 grasshoppers, *Locusta migratoria* (males). After 5 minutes the brains were dissected in phosphate buffered saline (PBS) according to Mokri-Moayyed et al. (2008). Three brains were placed in each test tube and 100 µl distilled H2O and 80 µl perchloric acid (PCA) was added. The test tubes were placed in a sonicator and the brains were disintegrated by approximately 5 seconds of sonication. The samples containing the disintegrated brains were centrifuged for 5 minutes (10000 g at 4° C.). 100 µl of the supernatants were move to new test tubes and the average concentration of 27 ng/ml mianserin was measured by LCMS.

Example B

20 µl of a 9.8 mg/ml solution of mianserin was injected into 3 grasshoppers, *Locusta migratoria* (males). After 15 minutes the brains were dissected in phosphate buffered saline (PBS) according to Mokri-Moayyed et al. (2008). The three brains were placed in a test tube and 100 µl distilled H2O and 80 µl perchloric acid (PCA) was added. The test tube was placed in a sonicator and the brains were disintegrated by approximately 5 seconds of sonication. The sample containing the disintegrated brains was centrifuged for 5 minutes (10000 g at 4° C.). 100 µl of the supernatant was move to a new test tube and the concentration of 73 ng/ml mianserin was measured by LCMS.

Example C

20 µl of a 9.8 mg/ml solution of mianserin was injected into 6 grasshoppers, *Locusta migratoria* (males). After 5 minutes the brains were dissected in phosphate buffered saline (PBS) according to Mokri-Moayyed et al. (2008). The brains were washed once in PBS. Three brains were placed in each test tube and 100 µl distilled H2O and 80 µl perchloric acid (PCA) was added. The test tubes were placed in a sonicator and the brains were disintegrated by approximately 5 seconds of sonication. The samples containing the disintegrated brains were centrifuged for 5 minutes (10000 g at 4° C.). 100 µl of the supernatants were move to new test tubes and the average concentration of 10 ng/ml mianserin was measured by LCMS.

Example D

20 µl of a 9.8 mg/ml solution of mianserin was injected into 3 grasshoppers, *Locusta migratoria* (males). After 15 minutes the brains were dissected in phosphate buffered saline (PBS) according to Mokri-Moayyed et al. (2008). The brains were washed once in PBS. The three brains were placed in a test tube and 100 µl distilled H2O and 80 µl perchloric acid (PCA) was added. The test tube was placed in a sonicator and the brains were disintegrated by approximately 5 seconds of sonication. The sample containing the disintegrated brains was centrifuged for 5 minutes (10000 g at 4° C.). 100 µl of the supernatant was move to a new test tube and a concentration of 97 ng/ml mianserin was measured by LCMS.

Example E

20 µl of a 9.8 mg/ml solution of mianserin was injected into 6 grasshoppers, *Locusta migratoria* (males). After 5 minutes the brains were dissected in phosphate buffered saline (PBS) according to Mokri-Moayyed et al. (2008). The brains were washed twice in PBS. Three brains were placed in each test tube and 100 µl distilled H2O and 80 µl perchloric acid (PCA) was added. The test tubes were placed in a sonicator and the brains were disintegrated by approximately 5 seconds of sonication. The samples containing the disintegrated brains were centrifuged for 5 minutes (10000 g at 4° C.). 100 µl of the supernatants were move to new test tubes and the average concentration of 32 ng/ml mianserin was measured by LCMS.

The studies in Example A-G show that there is an increase in mianserin brain concentration from 5 to 15 minutes and this is explained by a longer time of exposure, (c.f. Example G-I). Moreover, it can be concluded that washing of the brain do not lead to any significant reduction of the brain concentration.

Example F

20 µl of a 9.8 mg/ml solution of mianserin was injected into 9 grasshoppers, *Locusta migratoria* (males). After 5 minutes a cut was made through the frontal part of the locust head comprising the most frontal parts including the antennae, the compound eyes, the brain and all neural connections between the brain and the antennae and the eyes. The brain was then dissected in phosphate buffered saline (PBS) containing Evans Blue. The neural lamella was removed and three brains were placed in each test tube and 100 µl distilled H2O and 80 µl perchloric acid (PCA) was added. The test tubes were placed in a sonicator and the brains were disintegrated by approximately 5 seconds of sonication. The samples containing the disintegrated brains were centrifuged for 5 minutes (10000 g at 4° C.). 100 µl of the supernatants were move to new test tubes and the average concentration of 9 ng/ml mianserin was measured by LCMS.

Example F shows that mianserin penetrates the blood brain barrier (BBB) in grasshoppers and this reflects the BBB penetration in vertebrates. From example A-F it can be concluded that some of the compound binds to the neural lamella. Thus, the measured brain concentration has to be corrected for this contribution before the BBB penetration can be concluded. As an alternative the neural lamella can be removed and the brain concentration is then a direct measurement for the BBB penetration.

Example G

40 µl of a 8.8 mg/ml solution of mianserin in 5% DMSO was injected into 18 grasshoppers, *Locusta migratoria* (males). After 5 minutes 20 µl of hemolymph was extracted from each locust. A cut was made through the frontal part of the locust head comprising the most frontal parts including the antennae, the compound eyes, the brain and all neural connections between the brain and the antennae and the eyes. The brain was then dissected in saline containing Evans Blue.

2 hemolymph samples were placed in a test tube containing 60 µl of distilled H2O and 200 µl acetonitrile. Each sample was centrifuged for 5 minutes (10000 g at 4° C.). 100 µl of the supernatants were move to new test tubes and the average concentration of 38 µg/ml mianserin was measured by LCMS.

Each brain was washed in saline and placed in a test tube containing 100 µl distilled H2O. The neural lamella was removed and 6 brains were placed in each test tube and 200 µl acetonitrile was added. The test tubes were placed in a sonicator and the brains were disintegrated by approximately 5 seconds of sonication. The samples containing the disintegrated brains were centrifuged for 5 minutes (10000 g at 4° C.). 100 µl of the supernatants were move to new test tubes and the average concentration of 152 ng/ml mianserin was measured by LCMS.

Example H

40 µl of a 8.8 mg/ml solution of mianserin in 5% DMSO was injected into 18 grasshoppers, *Locusta migratoria* (males). After 15 minutes 20 µl of hemolymph was extracted from each locust. A cut was made through the frontal part of the locust head comprising the most frontal parts including the antennae, the compound eyes, the brain and all neural connections between the brain and the antennae and the eyes. The brain was dissected in saline containing Evans Blue.

2 hemolymph samples were placed in a test tube containing 60 µl of distilled H2O and 200 µl acetonitrile. Each sample was centrifuged for 5 minutes (10000 g at 4° C.). 100 µl of the supernatants were move to new test tubes and the average concentration of 17 µg/ml mianserin was measured by LCMS.

Each brain was washed in saline and placed in a test tube containing 100 µl distilled H2O. The neural lamella was removed and 6 brains were placed in each test tube and 200 µl acetonitrile was added. The test tubes were placed in a sonicator and the brains were disintegrated by approximately 5 seconds of sonication. The samples containing the disintegrated brains were centrifuged for 5 minutes (10000 g at 4° C.). 100 µl of the supernatants were move to new test tubes and the average concentration of 305 ng/ml mianserin was measured by LCMS.

Example I

40 µl of a 8.8 mg/ml solution of mianserin in 5% DMSO was injected into 18 grasshoppers, *Locusta migratoria* (males). After 45 minutes 20 µl of hemolymph was extracted from each locust. A cut was made through the frontal part of the locust head comprising the most frontal parts including the antennae, the compound eyes, the brain and all neural connections between the brain and the antennae and the eyes. The brain was dissected in saline containing Evans Blue.

2 hemolymph samples were placed in a test tube containing 60 µl of distilled H2O and 200 µl acetonitrile. Each sample was centrifuged for 5 minutes (10000 g at 4° C.). 100 µl of the supernatants were move to new test tubes and the average concentration of 13 µg/ml mianserin was measured by LCMS.

Each brain was washed in saline and placed in a test tube containing 100 µl distilled H2O. The neural lamella was removed and 6 brains were placed in each test tube and 200 µl acetonitrile was added. The test tubes were placed in a sonicator and the brains were disintegrated by approximately 5 seconds of sonication. The samples containing the disintegrated brains were centrifuged for 5 minutes (10000 g at 4° C.). 100 µl of the supernatants were move to new test tubes and the average concentration of 393 ng/ml mianserin was measured by LCMS.

From Example G-I it can be concluded that the hemolymph concentration of mianserin reduces with time while the brain concentration increases from 5-15 minutes and levels out from 15-45 minutes. This reflects the situation in vertebrates where a longer brain exposure increases the brain level until a certain limit. Moreover, the compound clearance in the vertebrate brain is slower than in the body fluid, i.e. exactly as it is seen in example G-I.

Example J

20 µl of a 630 µg/ml solution of serotonin was injected into 6 grasshoppers, *Locusta migratoria* (males). After 5 minutes 20 µl of hemolymph was extracted from each locust. A cut was made through the frontal part of the locust head comprising the most frontal parts including the antennae, the compound eyes, the brain and all neural connections between the brain and the antennae and the eyes and the brain was dissected in saline. Each hemolymph sample was placed in a test tube containing 80 µl of distilled H2O and 200 µl acetonitrile. Each sample was centrifuged for 5 minutes (10000 g at 4° C.). 100 µl of the supernatants were move to new test tubes and the average concentration of 4.7 µg/ml serotonin was measured by LCMS.

Each brain was washed in saline and placed in a test tube containing 100 µl distilled H2O. Three brains were placed in each test tube and 200 µl acetonitrile was added. The test tubes were placed in a sonicator and the brains were disintegrated by approximately 5 seconds of sonication. The samples containing the disintegrated brains were centrifuged for 5 minutes (10000 g at 4° C.). 100 µl of the supernatants were move to new test tubes and the average concentration of 86.5 ng/ml serotonin was measured by LCMS.

Example K 3 brains from Grasshoppers, *Locusta migratoria* (males), were used to measure the endogenous serotonin level in the brain. A cut was made through the frontal part of the locust head comprising the most frontal parts including the antennae, the compound eyes, the brain and all neural connections between the brain and the antennae and the eyes and the brain was dissected in saline. Each brain was washed in saline and placed in a test tube containing 100 µl distilled H2O. Three brains were placed in one test tube and 200 µl acetonitrile was added. The test tube was placed in a sonicator and the brains were disintegrated by approximately 5 seconds of sonication. The sample containing the disintegrated brains was centrifuged for 5 minutes (10000 g at 4° C.). 100 µl of the supernatant was move to a new test tube and a concentration of 20 ng/ml serotonin was measured by LCMS.

Examples A-F showed that the measured concentration of mianserin is increased by a factor 3 when the neural lamella is included in the brain concentration measurement. It is reasonable to assume that the serotonin bound to neural lamella accounts for a similar contribution as in the mianserin studies. Thus, introducing a correction factor based on the mianserin experiments suggest that the actual measured serotonin brain concentration in Example J is close to the endogenous serotonin level measured in Example K.

From Example J and K it can be concluded that serotonin only penetrates the grasshopper BBB to a very low extend, if any at all. A very low BBB penetration of serotonin is also seen in vertebrates.

Example L

20 µl of a 8.4 mg/ml 5% DMSO solution of buspirone was injected into 6 grasshoppers, *Locusta migratoria* (males). After 5 minutes 20 µl of hemolymph was extracted from each locust. A cut was made through the frontal part of the locust head comprising the most frontal parts including the antennae, the compound eyes, the brain and all neural connections between the brain and the antennae and the eyes and the brain was dissected in saline. Each hemolymph sample was placed in a test tube containing 80 µl of distilled H2O and 200 µl acetonitrile. Each sample was centrifuged for 5 minutes (10000 g at 4° C.). 100 µl of the supernatants were move to new test tubes and the average concentration of 4.5 µg/ml buspirone was measured by LCMS.

Each brain was washed in saline and placed in a test tube containing 100 µl distilled H2O. Three brains were placed in each test tube and 200 µl acetonitrile was added. The test tubes were placed in a sonicator and the brains were disintegrated by approximately 5 seconds of sonication. The samples containing the disintegrated brains were centrifuged for 5 minutes (10000 g at 4° C.). 100 µl of the supernatants were move to new test tubes and an average concentration below 20 ng/ml buspirone was measured by LCMS.

It was obvious from this example that buspirone penetrates the grasshopper BBB, but it is in a much lower fraction than in the mianserin case. This result reflects the vertebrate BBB penetration where there is a much lower BBB penetration of buspirone than the corresponding penetration of mianserin.

References

Banerjee and Baht (2007), Neuron-Glial Interactions in Blood-Brain Barrier Formation *Annual Review of Neuroscience* 30: 235-258.

Di, L. and Kerns, E. H. (2003). Profiling drug-like properties in discovery research. *Current Opinion in Chemical Biology* 7, 402-408.

Gaertner, L. S., Murray, C. L., Morris, C. E. (1998). Transepithelial transport of nicotine and vinblastine in isolated malpighian tubules of the tobacco hornworm (*Manduca sexta*) suggests a P-glycoprotein-like mechanism. *The Journal of Experimental Biology* 201, 2637-2645.

Garberg, P. et al. (2005). In vitro models for the blood-brain barrier. *Toxicology in Vitro* 19, 299-334.

Goldsworthy, G et al. (2003) Adipokinetic hormone enhances nodule formation and phenoloxidase activation in adult locusts injected with bacterial lipopolysaccaride. J. Insect. Physiol., 49, 793-803.

Gullan, P. J and Cranston, P. S. (2000). The insects. An outline of entomology. Blackwell Science Ltd.

Marsh, J. L., and Thompson, L. M. (2004). Can flies help humans treat neurodegenerative diseases? *Bioessays* 26, 485-496.

Marsh, J. L. and Thompson, L. M. (2006). *Drosophila* in the Study of Neurodegenerative Disease. *Neuron* 52, 169-178.

Mokri-Moayyed, B et al., (2008). Development of a novel ex vivo insect model for studying virulence determinants of *Escherichia coli* K1. J. Medical Microbiol. 57, 106-110.

Pardridge, W. M. (2002). Drug and gene targeting to the brain with molecular Trojan horses. *Nature Reviews Drug Discovery* 1, 131-139

Ruiz-Garcia, A., Bermejo, M., Moss A. Casabo, V. G. (2007). Pharmacokinetics in drug discovery. *Journal of Pharmaceutical Sciences*, 1-37.

Schinkel, A. H. (1999). P-Glycoprotein, a gatekeeper in the blood-brain barrier. *Advanced Drug Delivery Reviews* 36, 179-194.

Summerfield, S. et al. (2005). Improving the In Vitro Prediction of In Vivo CNS Penetration: Integrating Permeability, Pgp Efflux and Free Fractions in Blood and Brain. *Journal of Pharmacology And Experimental Therapeutics*.

Turksen, K. and Troy, T.-C. (2004). Barriers built on claudins. *Journal of Cell Science* 117, 2435-2447.

Xia, C. Q., Xiao, G., Liu, N., Pimprale, S., Fox, L., Patten, C. J., Crespi, C. L., Miwa, G., Gan, L.-S. (2006). Comparison of Species Differences of P-Glycoproteins in Beagle Dog, Rhesus Monkey, and Human Using ATPase Activity Assays. *Molecular Pharmaceutics* 3 (1), 78-86.

The invention claimed is:

1. A method for assessing whether a chemical compound is transported across the blood brain barrier (BBB) of a vertebrate, said method comprising:
    administering the chemical compound to an insect having a BBB;
    incubating the insect;
    dissecting out the brain comprising an intact BBB from the insect;
    homogenizing the dissected brain; and
    measuring the concentration of the chemical compound in the homogenized brain material, wherein detecting a minimum threshold concentration of the chemical compound in the homogenized brain material indicates the chemical compound will transport across the BBB of the vertebrate.

2. The method of claim 1, comprising incubating the insect for a period of between 0.5 hour and 5 hours before dissecting the brains and quantitating the concentration of the administered chemical compound in the dissected brain.

3. The method of claim 1, wherein the dissection of the brains is performed immediately after sacrificing the insect.

4. The method of claim 1, wherein measuring the concentration of the chemical compound in the homogenized brain material is performed by liquid chromatography, mass spectrometry, LC/MC, C/MSMS, or HPLC.

5. The method according to claim 1 wherein the chemical compound is administered parenterally or perorally.

6. The method according to claim 1 further comprising determining body:brain chemical compound concentration gradients to assess BBB penetration of the chemical compound.

7. The method according to claim 6 comprising analyzing the body:brain chemical compound concentration gradients to assess whether the chemical compound is metabolized by the blood brain barrier.

8. The method according to claim 1 wherein the vertebrate is a mammal.

9. The method according to claim 8 wherein the mammal is a human.

* * * * *